_United States Patent_ [19]

Grudzinskas et al.

[11] 4,415,501

[45] Nov. 15, 1983

[54] ALKENYLZIRCONIUM REAGENTS USEFUL FOR PROSTAGLANDIN ANALOG SYNTHESIS

[75] Inventors: Charles V. Grudzinskas, Upper Nyack, N.Y.; Guenter W. Nachtigall, Georgetown, Conn.

[73] Assignee: American Cyanamid Company, Stamford, Conn.

[21] Appl. No.: 331,373

[22] Filed: Dec. 16, 1981

[51] Int. Cl.$^3$ .................................................. C07F 7/00
[52] U.S. Cl. .................................. 260/429.3; 549/356
[58] Field of Search ....................................... 260/429.3

[56] References Cited

U.S. PATENT DOCUMENTS 4,125,567 11/1978 Kidwell et al. .................. 260/429.3
4,147,709 4/1979 Lynch .............................. 260/429.3
4,151,186 4/1979 Kidwell et al. .................. 260/429.3

OTHER PUBLICATIONS

Hart et al., JACS 96, 8115–8116, (1974).

J. Schwartz, et al., J. Amer. Chem. Soc., 102, 1333, (1980).

_Primary Examiner_—Helen M. S. Sneed
_Attorney, Agent, or Firm_—Robert P. Raymond

[57] ABSTRACT

Alkenylzirconium reagents of the general structural formula IX,

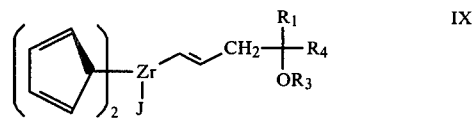

are useful in the syntheses of prostaglandin analogs. In the preceding structural formula J is bromo or chloro, $R_1$ is hydrogen, methyl, ethyl, vinyl, 1-propenyl, or cyclopropyl, $R_4$ is alkyl of 2–7 carbon atoms, and $R_3$ is a protecting group such as tetrahydropyranyl, 1-ethoxyethyl, or $C_1$–$C_4$-trialkylsilyl.

27 Claims, No Drawings

ALKENYLZIRCONIUM REAGENTS USEFUL FOR PROSTAGLANDIN ANALOG SYNTHESIS

BACKGROUND OF THE INVENTION

The prostaglandins are currently of great interest because of the broad physiological responses which they elicit in animals, including man.

Development of the potential application of both natural and synthetic prostaglandins relies upon efficient chemical synthetic methods being available. See, Mitra, "The Synthesis of Prostaglandins", Wiley, N.Y. 1977.

Processes for preparing prostaglandins and their analogs via conjugate addition of an alkenyl moiety to the unsaturated ketone functionality of a substituted cyclopentenone have been described in U.S. Pat. Nos. 3,965,143, 3,950,406 and 4,233,231, and Tet. Letters, 2063 (1977); Prostaglandins, 10,733 (1975) and J. Amer. Chem. Soc., 97, 857 (1975). Such reactions usually involve the use of alkenyl lithium compounds as intermediates in the formation of alkenylcuprates, the latter being capable of the desired conjugate addition reaction. Extensive research has been done aimed at developing species which could duplicate beneficial aspects of cuprate chemistry while not relying on lithium reagent precursors. Implementation of lithium-based cuprate processes is often hampered by the tedious preparation of these organolithium precursors. In the special case of alkenylcuprates, important to the synthesis of various natural products, it is necessary to generate and maintain stereochemically pure alkenyl species. Alkenyllithium reagents used to prepare the corresponding cuprates are obtained by metal-halogen exchange with the corresponding alkenylhalide or by reaction of these organic halides with lithium metal. Although the conversion of alkenylhalides to alkenyllithium reagents occurs predominantly with retention of configuration, some loss of double-bond stereochemistry can occur. Lastly, alkenylcuprate species are generally utilized at low temperatures since they are thermally unstable.

The possibility of activating organozirconium species toward conjugate addition using a second metallic species catalytically, and the use of the activated species for the synthesis of 15-hydroxy prostaglandin analogs were realized by J. Schwartz, et al., J. Amer. Chem. Soc. 102 1333 (1980). However, the prior art does not disclose an organozirconium species useful in a conjugate addition reaction directed to the preparation of 15-deoxy-16-hydroxy-16-substituted prostaglandins.

DETAILED DESCRIPTION OF THE INVENTION

Alkenylzirconium reagents of the formula IX:

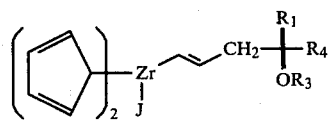

IX where J is bromo or chloro, $R_1$ is hydrogen, methyl, ethyl, vinyl, 1-propenyl or cyclopropyl; $R_4$ is alkyl of 2–7 carbon atoms, and $R_3$ is a hydroxyl-protecting group such as tetrahydropyranyl (THP), 1-ethoxyethyl, or $C_1$–$C_4$ trialkylsilyl; are useful as key intermediates in a conjugate addition process with racemic or optically active 2-cyclopenten-1-ones of the general formula IV:

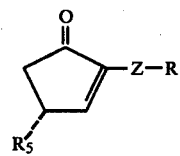

IV where R is $CO_2R_8$ wherein $R_8$ is $C_1$–$C_6$ alkyl or a protecting group such as tetrahydropyranyl, 1-ethoxyethyl, or $C_1$–$C_4$-trialkylsilyl; or is a protected hydroxymethylcarbonyl moiety such as:

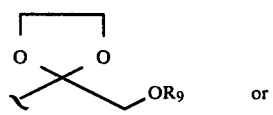

or

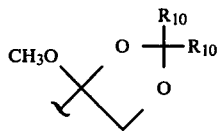

where $R_9$ is trimethylsilyl or triethylsilyl, and $R_{10}$ is methyl or ethyl; Z is —$(CH_2)_n$— or

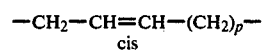

where n is 5–7 (preferably 6) and p is 2–4 (preferably 3); and $R_5$ is hydrogen, tetrahydropyranyloxy, 1-ethoxyethoxy, $C_1$–$C_4$-trialkylsiloxy or $OC(R_{10})_2OCH_3$ where $R_{10}$ is methyl or ethyl. The conjugate addition reaction, followed by removal of the protecting groups by exposure of the crude reaction mixture to dilute aqueous acid affords pharmaceutically useful racemic or optically-active analogs of the general formula X:

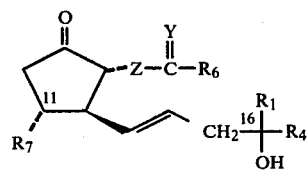

X where $R_6$ is —$CH_2OH$, hydroxy, or alkoxy of one to six carbon atoms; $R_7$ is H or hydroxy, Y is —$OCH_2CH_2O$— or O, and Z, $R_1$ and $R_4$ are as hereinabove defined.

Formula X is represented as having the R configuration at $C_{11}$ and the RS configuration at $C_{16}$. Optically-pure prostaglandins of the type X of the 11R, 16S or 11R, 16R configuration are obtained by employing optically-pure cyclopentenones of structure IV-R:

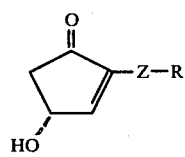

IV-R where Z and R are as described hereinabove, which are protected and reacted with racemic alkenylzirconium reagents of type IX in the conjugate addition reaction. In such a reaction it is believed that the lower side chain enters in an orientation trans to the $C_{11}$-hydroxy and trans to the α-side chain of the cyclopentenone ring. Deprotection of the crude reaction mixture yields mixtures consisting of prostaglandin analogs of the general formulae:

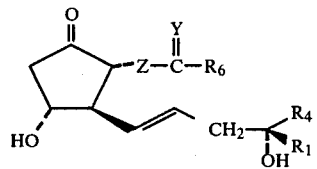
X-S and

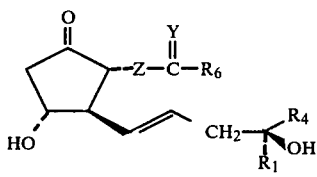
X-R where $R_6$, Y, Z, $R_1$ and $R_4$ are as hereinabove described and which may be separated by careful chromatographic techniques. If optically-pure cyclopentenones of the structure IV-S:

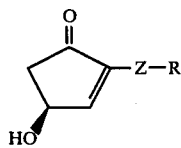
IV-S where Z and R are as hereinabove described, are protected and employed in the conjugate addition reaction, deprotection of the crude reaction mixture yields mixtures of optically-pure prostaglandin analogs of the general formulae:

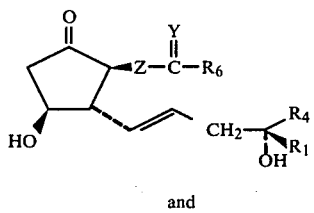
ent-X-S and

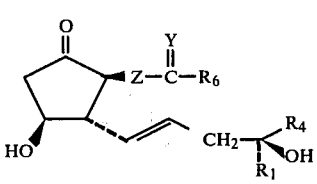
ent-X-R where $R_6$, Y, Z, $R_1$ and $R_4$ are as hereinabove described, and which may generally be separated by chromatography.

Racemic 4-hydroxy-1-alkynes may be resolved into optically-pure 4R- and 4S-hydroxy-1-alkynes by the general procedures of Examples 140–142 of U.S. Pat. No. 4,254,285, which is incorporated herein by reference. When an optically-pure 4-hydroxy-1-alkyne is protected and used to form the corresponding alkenylzirconium reagent which is in turn reacted with a cyclopentenone of type IV-S or IV-R, only one optically-pure prostaglandin analog is obtained, depending upon the particular alkenylzirconium-cyclopentenone pair chosen. For example, reaction of IV-R with the optically-pure zirconium reagent formed from protected 4-methyl-4S-hydroxy-1-octyne provides only optically-pure X-S wherein $R_1$ is methyl and $R_4$ is n-butyl after deprotection and optional chromatography.

If racemic cyclopentenones of the general formula IV-RS

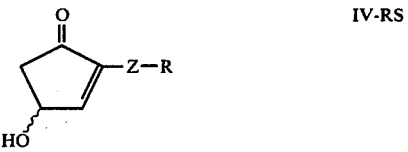
IV-RS where Z and R are as above described are protected and employed in the conjugate addition reaction with optically-pure alkenylzirconium reagents prepared as described above, deprotection of the crude reaction mixture yields prostaglandin analog pairs having either the 16R- or 16S- configuration in conjunction with a racemic center at C-11. For example, reaction of the optically-pure zirconium reagent formed from 4-methyl-4S-hydroxy-1-octyne with protected IV-RS, followed by deprotection of the crude reaction mixture affords optically-pure prostaglandin analogs of the general formulae:

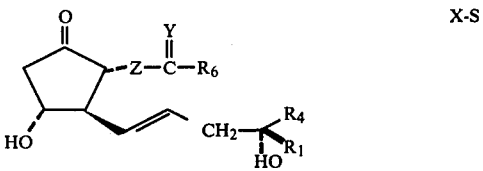
X-S and

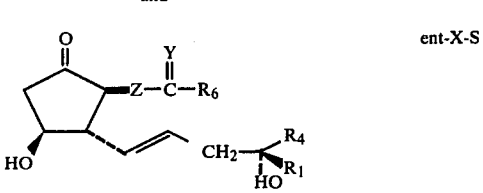
ent-X-S where Z, $R_6$ and Y are as hereinabove defined, $R_1$ is methyl and $R_4$ is n-butyl, which may be separated by careful chromatography. Thus, a pure analog incorporating any of the four possible combination of stereochemical configuration at $C_{11}$ and $C_{16}$ may be obtained by the appropriate combination of alkenylzirconium reagents of the type IX with protected cyclopentenones of type IV. Procedures for formation of 4S- and 4R-cyclopentenones of type IV are described in U.S. Pat. Nos. 4,254,285 and 4,061,670 which are incorporated herein by reference. If protected cyclopentenones of general formula IV-RS are employed in the conjugate addition reaction with racemic IX, a mixture of the racemic analog pairs dl-X-S and dl-ent-X-S is formed.

If cyclopentenones of type IV, wherein $R_5$ is H and Z and R are as hereinabove defined, are employed in the conjugate addition reaction with racemic IX, a mixture of two chromatographically separable, racemic pairs of prostaglandin analogs of formulae X-nat. and X-ent. type is obtained wherein $R_6$, Y, R, and $R_4$ are as hereinabove described, in which the 16-hydroxy substituent is of the RS configuration in each:

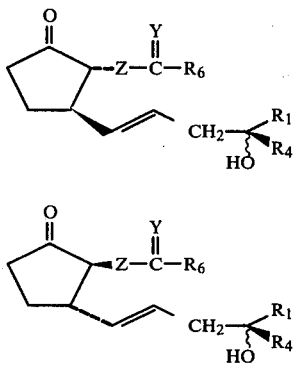

If optically-pure alkenylzirconium reagents are formed as described above and employed in the conjugate addition reaction, a mixture of two separable, optically-pure analogs of the type X-nat. and X-ent. is obtained both havng either the 16R- or 16S- configuration at C-16.

Flowchart A outlines a preferred procedure for preparing protected cyclopentenone compounds of structure IV, where Z and $R_{10}$ are as hereinabove defined.

Flowchart A
Synthetic Pathway for
Preparation of Compound IV

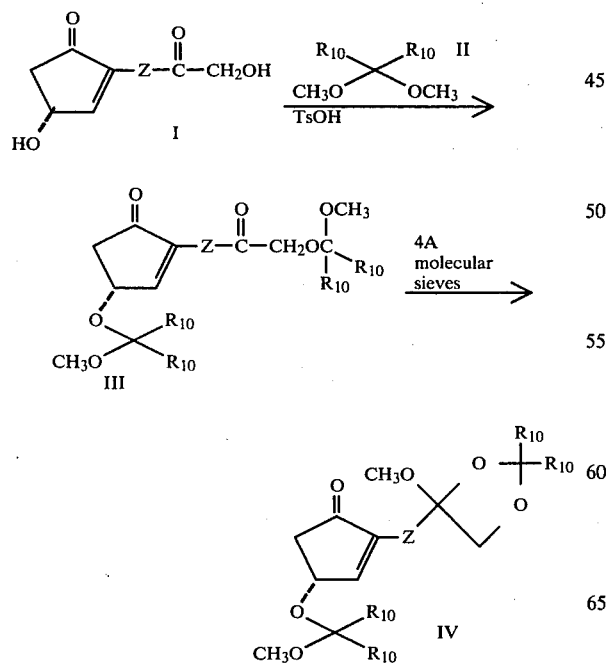

For example, treatment of cyclopentenone I, wherein Z is $-(CH_2)_6-$ with a large excess of 2,2-dimethoxypropane (II wherein $R_{10}$ is methyl) and a catalytic amount of para-toluene-sulfonic acid (TsOH) produces hemiketal IIIa where Z is $-(CH_2)_6-$ and $R_{10}$ is methyl. IIIa may be used in the conjugate addition reaction with alkenylzirconium reagents of type IX, or alternatively, may be rearranged to dioxolane IVa having Z and $R_{10}$ as defined above by treatment with 4A molecular sieves.

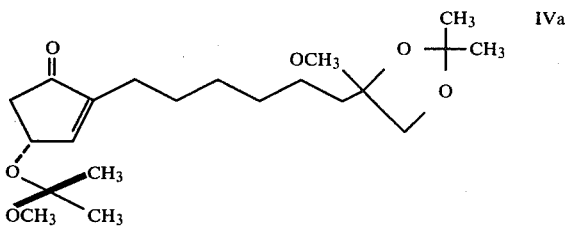

Intermediate IIIa wherein $R_{10}$=methyl and $Z=-(CH_2)_6$ is disclosed by U.S. Patent No. 4,254,485, which is incorporated herein by reference.

The final composition of the product as determined by $^{13}C$ nuclear magnetic resonance spectroscopy ("NMR") was 20% IIIa and 80% IVa. Pure IVa can be isolated by column chromatography using anhydrous solvents and activated silica gel. Pure IVa was found to be stable for several months when stored at 0° C. in an airtight container. In solution at 25° C., a slow, nonhydrolytic decomposition takes place.

3,3-diethoxypentane has been substituted for 2,2-dimethoxypropane in the above reaction sequence, affording compound IVb, wherein $R_{10}$ is ethyl and Z is $-CH=CH-(CH_2)_3-$ or $-(CH_2)_6-$: IVb
cis

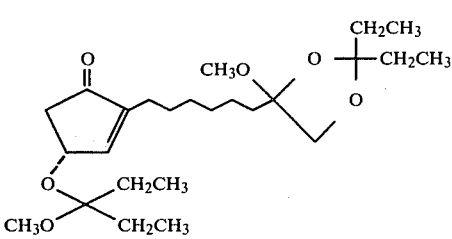

Other preferred cyclopentenone compounds of the type IV which may be employed include those depicted in Table I below. Each of the publications and U.S. patents listed under the caption "Ref." in Table I below is incorporated herein by reference.

TABLE I

Cyclopentenone Intermediates of Type IV

| Compound | Number | Ref. |
|---|---|---|
| 4-OTHP-2-(CH₂)₆CO₂CH₃ cyclopentenone | IVc | J. Amer. Chem. Soc. 95 1676 (1973) |
| 4-OTHP-2-(CH₂-CH=CH-(CH₂)₃CO₂CH₃) cyclopentenone | IVd | Tet. Let. 2312 (1973) |
| 2-(CH₂)₆CO₂CH₃ cyclopentenone | IVe | Tet. Let. 2435 (1972) |
| 2-(CH₂-CH=CH-(CH₂)₃CO₂CH₃) cyclopentenone | IVf | J. Org. Chem. 38 3413 (1973) |
| 2-[(CH₂)₅-C(OCH₂CH₂O)(CH₃)-CH₂-OSi(CH₃)₃] cyclopentenone | IVg | U.S. Pat. No. 4,254,285 |
| 4-OSi(CH₃)₂-2-[CH₂-C≡C-(CH₂)₂-C(OCH₂CH₂O)(CH₃)-CH₂-OSi(CH₃)₃] cyclopentenone | IVh | U.S. Pat. No. 4,254,285 |
| 4-[OC(CH₃)(OCH₃)CH₃]-2-[CH₂-CH=CH-(CH₂)₂-C(O)-CH₂-OC(OCH₃)(CH₃)₂] cyclopentenone | IIIb | U.S. Pat. No. 4,254,285 |
| 4-[OC(CH₃)(OCH₃)CH₃]-2-[(CH₂)₅-C(O)-CH₂-OC(CH₃)₂(OCH₃)] cyclopentenone | IIIa | U.S. Pat. No. 4,254,485 |

Flowchart B outlines the preparation of the preferred dicyclopentadienylzirconium chloride (VIII), and its reaction with a protected alkynol of type VI wherein $R_1$, $R_3$, and $R_4$ are as hereinabove defined.

Flowchart B
Synthetic Pathway for Preparation of Compound IX

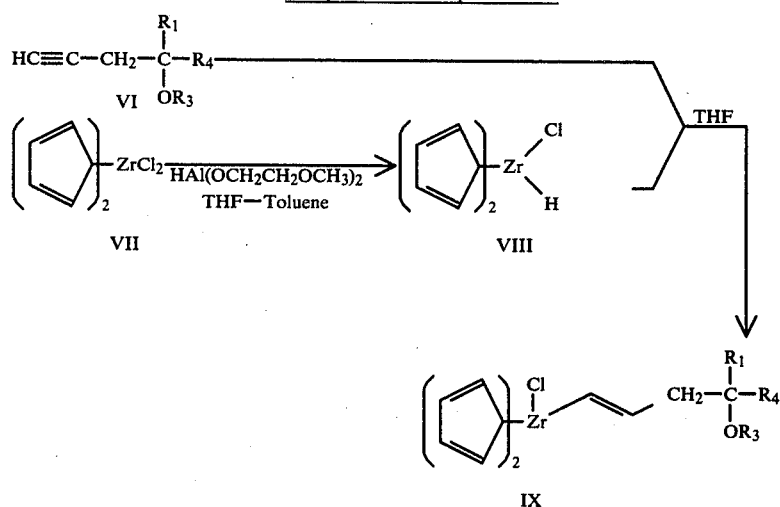

Dicyclopentadienyl zirconium chlorohydride VIII, the hydrozirconation reagent, is available commercially, but is expensive and hard to handle, since it is light and air-moisture sensitive. It has been found more satisfactory to generate the reagent in situ by the reduction of dicyclopentadienyl zirconium dichloride (VII) to zirconium chlorohydride VIII. The reduction is preferably accomplished by dissolving VII in tetrahydrofuran (THF) and adding an equivalent of Vitride ® reducing agent, bis-(2-methoxyethoxy) aluminum hydride (70% solution in toluene), under an inert atmosphere. The resulting precipitate of VIII is washed and solvents removed by vacuum filtration under argon pressure. The solid VIII (71–78% yield) is resuspended in THF and a protected alkynol VI, wherein $R_1$, $R_3$ and $R_4$ are as hereinabove defined, is added to the stirred suspension at 20°–30° C. The reaction is complete after 20–30 minutes and the resultant solution of IX, where $R_1$, $R_3$ and $R_4$ are as hereinabove defined, is filtered into another reaction vessel under argon. The following summarizes the $^{13}$C-NMR spectrum of a preferred embodiment of reagent IX, IXa, obtained in benzene-d$_6$. (Carbon-13 Chemical shifts [ppm from tetramethyl-silane] for the Zirconium Alkenyl Reagent IXa in Benzene-d$_6$):

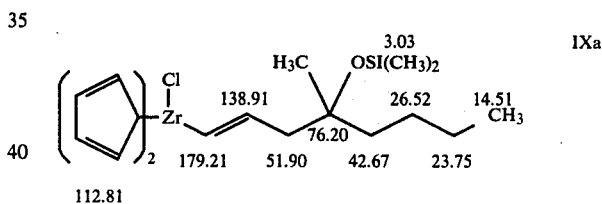

Due to moisture-sensitivity of the reagent, it is best prepared just prior to use.

The alkenylzirconium reagents of type IX wherein $R_1$, $R_3$ and $R_4$ are as hereinabove defined are reacted with 2-cyclopenten-1-ones of type IV wherein $R_5$ is H (branch A) or protected hydroxy (branch B), and Z and R are as hereinabove defined, in the presence of a catalytic amount of a reduced nickel catalyst. The crude products are treated with dilute aqueous acid to yield prostaglandin analog mixtures of type X, wherein $R_1$, $R_4$, $R_6$, Y and Z are as above defined. These reactions are outlined in Flowchart C. Chromatography of X mixtures as described above allows isolation of pure isomer pairs X-R and X-S, X-ent. and X-nat.

Flowchart C
Conjugate Addition Reaction

-continued
Flowchart C
Conjugate Addition Reaction

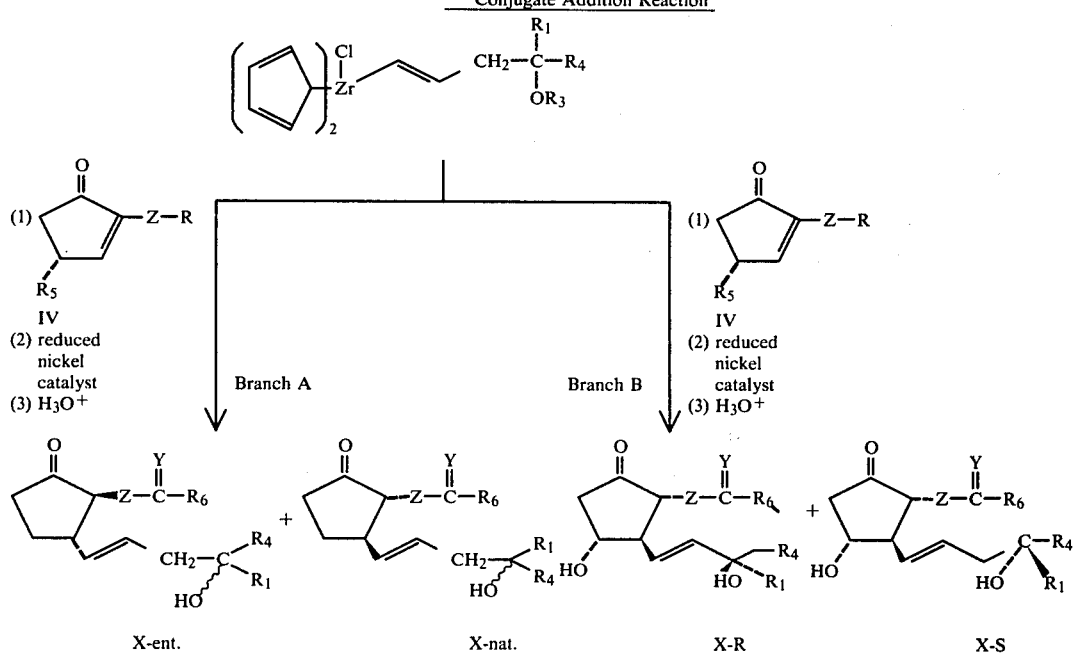

Table II summarizes preferred embodiments of the conjugate addition reaction, showing the results of a number of reactions between IXa and racemic IVa in the presence of reduced nickel catalyst, followed by deprotetction of crude adduct to yield racemic analog Xa.

The reduced nickel catalyst is prepared as described in J. Schwartz, et al., J. Amer. Chem. Soc. 102 1333 (1980) which is incorporated herein by reference. When the combination is complete, the selected reaction temperature is established and the reaction is held at that temperature for the desired length of time. The reaction is

TABLE II

Conjugate Addition of IXa [structure shown] to IVa and Deprotection of the Adduct to Obtain Xa [structure shown]

| | Protecting Groups | | Reaction | | Deprotection with 3:1:1 HOAc:H₂O:THF | | | % Yield of Real Xa in | | | Purity (% Real Xa) of | |
|---|---|---|---|---|---|---|---|---|---|---|---|---|
| | | | Temp. | Time | ml/mmols | Neutralization | | | | | | |
| Reaction | R in IXa | R₁₀ in IVa | (°C.) | (hrs.) | (scale) | NaHCO₃ (equiv.) | NH₄OH (equiv.) | Crude Product | Hexane Insol's | Chromato-graphed | Hexane Insol's | Chromato-graphed |
| A | Et₃Si— | Me— | 8 | 19 | 7.8 | lrg. excess | — | — | 60.7 | 57.5 | 73.0 | 96.5 |
| B | Me₃Si— | Me— | 8 | 17 | 4.0 | — | 1 | — | 37.3 | — | 41.0 | — |
| C | Et₃Si— | Me— | 8 | 16 | 5.9 | 1 | — | — | 62.5 | — | 72.6 | — |
| | | | | | | | | — | 58.2 | — | 69.8 | — |
| D | Et₃Si— | Et— | 8 | 18 | 5.8 | — | 1 | — | 48.8 | — | 57.3 | — |
| E | Et₃Si— | Et— | 8 | 19 | 6.0 | — | 1 | 40.4 | 44.8 | — | 54.7 | — |
| F | Et₃Si— | Et— | 8 | 17 | 6.6 | — | 1 | 44.4 | — | — | — | — |
| G | Et₃Si— | Et— | 8 | 20 | 6.0 | — | 1 | 34.5 | 27.9 | — | 36.7 | — |
| H | Et₃Si— | Me | 8 | 18 | 6.5 | — | 1 | 49.9 | 49.9 | 36.0 | 64.7 | 106.8 |

The conjugate addition reaction is carried out by combining a mixture of IX with IV in an ethereal solvent, preferably THF, with a freshly prepared solution of pre-reduced nickel catalyst with ice bath cooling.

terminated by the addition of an aqueous solution of ammonium chloride. The crude products are isolated by extraction and, to remove the protecting groups, are treated with a deprotection medium consisting of dilute aqueous acid, preferably acetic acid, THF and water. The deprotected crude X is prepurified by treatment with hexane. Final purification and optional separation of analog pairs are accomplished by chromatography on silica gel or silicic acid-Celite ®.

In the following examples all glass apparatus used is dried at 140° C. for at least two hours, and then permitted to cool to 25° C. under argon prior to use. Solvents (tetrahydrofuran [THF], methylene chloride, hexane, ethyl acetate) are dried by adding a 30 ml bulk volume of activated 4A molecular sieves to each 1-pint bottle which is then provided with an argon atmosphere and sealed with a rubber septum. The bottles are allowed to stand for 3-4 days before use of the solvents.

Intermediates are identified by $^{13}$C-nuclear magnetic resonance ("NMR") spectroscopy. Assays of final product mixtures for their content of analog X are carried out by high pressure liquid chromatography techniques (HPLC) and based on quantification by comparison with standard samples. A 4.6×25 mm ZORBAX ODS (duPont) column is used in a Spectra-Physics Model 350B liquid chromatograph, eluting with methanol-acetonitrile-water in a ratio of 3:3:4 (v/v). Preparative HPLC is carried out using a Water's Associates Prep. LC/System 500 chromatograph equipped with Prep Pak 500/Silica columns, and eluting with ethyl-acetate-hexane-ethanol in a ratio of 160:40:3 (v/v).

Chromatographic silica gel or silicic acid is dehydrated by heating to 170°–180° for a minimum of 24 hours.

Nickel acetylacetonate hydrate (Aldrich Chemical Co.) is dehydrated by heating in vacuo for 18 hours at 90°–95° C. The dehydrated solid is dissolved in a quantity of anhydrous ethyl ether, then stirred for 1 hr. with anhydrous magnesium sulfate, then filtered. The ether is evaporated in vacuo to afford anhydrous nickel acetylacetonate as a green solid.

The invention will be described with reference to the following detailed examples.

EXAMPLE 1

Preparation of 4-methyl-4-triethylsilyloxy-1-octyne(VIa, $R_1$=methyl, $R_3$=triethylsilyl, $R_4$=n-butyl).

A solution of 175.8 g of 4-hydroxy-4-methyl-1-octyne (U.S. Pat. No. 4,233,231), 112.1 g of imidazole and 625 ml of dry dimethylformamide (DMF) was stirred under dry nitrogen and 207.9 g of triethylchlorosilane added. The resulting homogenous solution was stirred at 50°–55° for 19 hours, then cooled to 25° C. and partitioned between hexane and water. The hexane layer was washed three times with water, then dried over anhydrous magnesium sulfate (MgSO$_4$), and hexane evaporated in vacuo. The concentrate was distilled to yield 94.7% of the title compound as a colorless liquid, bp 60°–61° C. (0.20 mm Hg).

EXAMPLES 2-6

The 4-hydroxy-1-alkynes of Table III which are disclosed in U.S. Pat. No. 4,254,285 are converted into the 4-protected-1-alkynes of the table by the procedure of Example 1.

TABLE III

| Ex. | 4-hydroxy-1-alkyne | 4-Protected-1-alkyne |
|---|---|---|
| 2 | 5,5-dimethyl-4-hydroxy-1-octyne | 5,5-dimethyl-4-triethylsiloxy-1-octyne |
| 3 | 4-cyclopropyl-4-hydroxy-1-octyne | 4-cyclopropyl-4-triethylsiloxy-1-octyne |
| 4 | 4-(1-propenyl)-4-hydroxy-1-octyne | 4-(1-propenyl)-4-triethylsiloxy-1-octyne |
| 5 | 4-vinyl-4-hydroxy-1-octyne | 4-vinyl-4-triethylsiloxy-1-octyne |
| 6 | 4-ethyl-4-hydroxy-1-octyne | 4-ethyl-4-triethylsiloxy-1-octyne |

EXAMPLE 7

Preparation of 1-(2,2-Dimethyl-4-methoxy-1,3-dioxolan-4-yl)-7-[3R-(1-methoxy-1-methylethoxy)-5-oxocyclopent-1-en-yl]-hexane IVa.

In a 1000 ml reaction flask equipped with a mechanically driven stirrer and in which an atmosphere of dry argon was maintained were combined 24.0 of I (Z=—(CH$_2$)$_6$—) (U.S. Pat. No. 4,254,485) and 350 ml of 2,2-dimethoxypropane (II, R$_{10}$=methyl). To the resultant stirred suspension was added 475 mg of p-toluene-sulfonic acid (TsOH), and the yellow solution stirred for 90 min. at 25° C. A bulk volume of 135 ml of activated 4A molecular sieves was introduced and stirring continued for 5 hours. Anhydrous potassium carbonate (300 mg) was added and stirring continued for 50 minutes. The reaction mixture was filtered under argon pressure. The residue of molecular sieves was washed 2–3 times with 50–70 ml of 2,2-dimethoxypropane and the filtered wash solutions combined with the original filtrate. Evaporation of solvents yielded 34–36 g of a 4–1 mixture of IVa and IIIa (R$_{10}$=methyl, Z=—(CH$_2$)$_6$—) (90–95% yield). Chromatography on silica gel with ethyl acetate-hexane mixtures yielded pure title compound in 55–65% yield, pure by C$^{13}$-NMR.

EXAMPLE 8

Preparation of 1-(2,2-Diethyl-4-methoxy-1,3-dioxolan-4-yl)-7-[3R-(1-methoxy-1-ethylpropoxy)-5-oxo-1-cyclopent-1-enyl]hexane IVb.

Repeating in a similar manner the procedure of Example 2 above, but replacing 2,2-dimethoxypropane with 3,3-diethoxypentane yields the title compound IVb.

EXAMPLES 9-14

The cyclopentenones of the table which are disclosed in U.S. Pat. No. 4,254,285, are converted into the protected cyclopentenones of the table by the procedures of Examples 7 or 8.

TABLE IV

| | Protected Cyclopentenones | | |
|---|---|---|---|
| Ex. | Cyclopentenones | Procedure of Example | Protected Cyclopentenone |
| 9 | 1-hydroxy-8-(5-oxocyclo-penten-1-yl)octan-2-one | 7 | 1-(2,2-dimethyl-4-methoxy-1,3-dioxolan-4-yl)-6-(5-oxocyclo-pent-1-enyl)hexane |
| 10 | 1-hydroxy-8-(5-oxocyclo-penten-1-yl)octan-2-one | 8 | 1-(2,2-diethyl-4-methoxy-1,3-dioxolan-4-yl)-6-(5- |

TABLE IV-continued

Protected Cyclopentenones

| Ex. | Cyclopentenones | Procedure of Example | Protected Cyclopentenone |
|---|---|---|---|
| 11 | 1-hydroxy-8-(5-oxocyclopenten-1-yl)oct-6-cis-en-2-one | 7 | 1-(2,2-dimethyl-4-methoxy-1,3-dioxolan-4-yl)-6-(5-oxocyclopent-1-enyl)hex-4-cis-ene. |
| 12 | 1-hydroxy-8-(5-oxocyclopenten-1-yl)oct-6-cis-en-2-one | 8 | 1-(2,2-diethyl-4-methoxy-1,3-dioxolan-4-yl)-6-(5-oxocyclopen-1-enyl)-hex-4-cis-ene. |
| 13 | 1-hydroxy-8-(3R—hydroxy-5-oxo-cyclopenten-1-yl)-oct-6-cis-en-2-one | 7 | 1-(2,2-dimethyl-4-methoxy-1,3-dioxolan-4-yl)-6-[3R—(1-methoxy-1-methylethoxy)-5-oxocyclopent-1-enyl]-hex-4-cis-ene. |
| 14 | 1-hydroxy-8-(3R—hydroxy-5-oxo-cyclopenten-1-yl)oct-6-cis-en-2-one | 8 | 1-(2,2-diethyl-4-methoxy-1,3-dioxolan-4-yl)-6-[3R—(1-methoxy-1-ethylpropoxy)-5-oxo-1-cyclopent-1-enyl]hex-4-cis-ene |

EXAMPLE 15

Preparation of chloro-bis($\eta^5$-2,4-cyclopentadien-1-yl)-(4-methyl-4-triethylsiloxy-1-trans-octenyl)zirconium(IXa, $R_1$=methyl, $R_3$=triethylsilyl, $R_4$=n-butyl).

A 2 l, round-bottomed reaction flask fitted with a fritted-glass filter was charged with 63.1 g of dichloro-bis-($\eta^5$-2,4-cyclopentadien-1-yl)zirconium (Alfa-Ventron) under argon, followed by addition of 650 ml of dry tetrahydrofuran (THF). To the resulting solution was added slowly via syringe 30.2 ml of 3.58 M bis(2-methoxy-ethoxy) aluminum hydride in toluene (Vitride ® reducing agent) (Realco), with external cooling as necessary to maintain a reaction temperature of 25° C. The resulting suspension of VIII was stirred an additional 30 min., filtered, and the white residue washed three times with 215 ml of dry THF. The washed residue, VIII, was resuspended in 650 ml of dry THF in the original flask. Into the stirred suspension was injected 45.3g of 4-methyl-4-triethylsiloxy-1-octyne VIa. The reaction mixture was stirred for 30 min. at 25° C. to complete the formation of a solution of the title compound which was used as described in Example 27.

EXAMPLES 16–21

The 4-protected-1-alkynes of the table which are disclosed in U.S. Pat. No. 4,254,385 and those of Table III are converted into the alkenylzirconium reagents of the table by the procedure described in Example 15.

TABLE V

| | | Zirconium Reagents |
|---|---|---|
| Ex. | Protected 4-Hydroxy-1-Alkyne (IV) | Chloro-bis($\eta^5$-2,4-cyclopentadienyl)-(4-protected-1-trans-alkenyl)-zirconium (IX) |
| 16 | 5,5-dimethyl-4-trimethylsiloxy-1-octyne | chloro-bis($\eta^5$-2,4-cyclopentadien-1-yl)-(5,5-dimethyl-4-trimethylsiloxy-1-trans-octenyl)zirconium |
| 17 | 4-methyl-4-trimethylsiloxy-1-octyne | chloro-bis($\eta^5$-2,4-cyclopentadien-1-yl)-(4-methyl-4-trimethylsiloxy-1-trans-octenyl)zirconium |
| 18 | 4-cyclopropyl-4-trimethylsiloxy-1-octyne | chloro-bis($\eta^5$-2,4-cyclopentadien-1-yl)-(4-cyclopropyl-4-trimethylsiloxy-1-trans-octenyl)zirconium |
| 19 | 4-(1-propenyl)-4-trimethylsiloxy-1-octyne | chloro-bis($\eta^5$-2,4-cyclopentadien-1-yl)-[4-(1-propenyl)-4-trimethylsiloxy-1-trans-octenyl]zirconium |
| 20 | 4-vinyl-4-trimethylsiloxy-1-octyne | chloro-bis($\eta^5$-2,4-cyclopentadien-1-yl)-(4-vinyl-4-trimethylsiloxy-1-trans-octenyl)zirconium |
| 21 | 4-ethyl-4-trimethylsiloxy-1-octyne | chloro-bis($\eta^5$-cyclopentadien-1-yl)-(4-ethyl-4-trimethylsiloxy-1-trans-octenyl)zirconium |
| 22 | Ex. 2 | chloro-bis($\eta^5$-2,4-cyclopentadien-1-yl)-(5,5-dimethyl-4-triethylsiloxy-1-trans-octenyl)zirconium |
| 23 | Ex. 3 | chloro-bis($\eta^5$-2,4-cyclopentadien-1-yl)-(4-cyclopropyl-4-triethylsiloxy-1-trans-octenyl)zirconium |
| 24 | Ex. 4 | chloro-bis($\eta^5$-2,4-cyclopentadien-1-yl)-[4-(1-propenyl)-4-triethylsiloxy-1-trans-octenyl]zirconium |
| 25 | Ex. 5 | chloro-bis($\eta^5$-2,4-cyclopentadien-1-yl)-(4-vinyl-4-triethylsiloxy-1-trans-octenyl)zirconium |
| 26 | Ex. 6 | chloro-bis($\eta^5$-2,4-cyclopentadien-1-yl)-(4-ethyl-4-triethylsiloxy-1-trans-octenyl)zirconium |

EXAMPLE 27

Preparation of 1-hydroxymethyl-1,9-dioxo-11R, 16S-dihydroxy-16-methylprost-13-trans-ene(Xa-S) and 1-hydroxymethyl-1,9-dioxo-11R, 16-dihydroxy-16-methylprost-13-trans-ene(Xa-R).

A solution of 5.5 g of anhydrous nickel acetylacetonate in 650 ml of dry THF was stirred under argon, cooled to 0° C. and 21.6 ml of 1 M diisobutylaluminum hydride in hexane (Aldrich Chemical Co). injected.

A solution of chloro-bis($\eta^5$-2,4-cyclopentadien-1-yl)-(4-methyl-4-triethylsiloxy-1-trans-octenyl)zirconium, IXa, $R_1$=methyl, $R_3$=triethylsilyl, $R_4$=n-butyl, freshly prepared as described in Example 15, was combined with 41.5 g of 1-(2,2-diethyl-4-methoxy-1,3-dioxolan-4-yl)-6-[3RS-(1-methoxy-1-ethylpropoxy)-5-oxo-cyclopenten-1-yl]hexane IVb-RS in 430 ml of dry THF. This solution was cooled to 0° C. and added to the stirred solution of prereduced nickel catalyst over 35 min. The reaction flask was cooled to 8° C. with external cooling and the mixture stirred under argon for 18 hours. Saturated aqueous ammonium chloride (1750 ml) was added and the reaction mixture stirred 50 minutes. The organic phase was added to 3.7 l of stirred hexane. The mixture was filtered, the filtrate dried over anhydrous magnesium sulfate, then filtered and evaporated to yield 83.5 g of an oil.

The oil was stirred with a mixture of 420 ml glacial acetic acid, 140 ml of THF and 140 ml of water for 5.0 hours at 25° C. The reaction mixture was cooled in an ice bath and one liter of ethyl ether was added, followed by 407 g of 29.9% aqueous ammonia (NH$_4$OH) in 648 ml of water. The ether layer was isolated and dried over anhydrous magnesium sulfate with added sodium bicarbonate (NaHCO$_3$). The ether solution was filtered and evaporated in vacuo to yield 68.0 g of a crude mixture of the title compounds as a viscous oil (162%, 30.3% pure by HPLC assay).

A solution of 67.8 g of crude product in 100 ml of methyl ethyl ketone was added to 15.0 l of stirred hexane. The mixture was stirred for 1 hour. The hexane was removed by siphoning and the coalesced, viscous residue dissolved in 500 ml of methylene chloride. The solution was dried over anhydrous magnesium sulfate, filtered, and methylene chloride removed in vacuo to yield 76% of the title compounds (64.7% pure by HPLC assay). Further purification of the crude product was achieved by preparative HPLC. A solution of 31.6 g of crude product in 150 ml ethyl acetate was chromatographed in three runs to yield 13.8 g of a mixture of the pure racemic title compounds as a pale yellow oil which was identified by HPLC assay against a known sample and by spectral analysis. Use of 3R-IVb and application of further chromatography can be employed to isolate approximately equal portions of Xa-S and Xa-R.

EXAMPLES 28–60

The protected cyclopentenones Table I or Table IV are reacted with the alkenylzirconium reagents of Table V to yield the prostaglandin analogs (substituted prostanes) of the table by the procedures of Example 27.

TABLE VI

| Ex. | Protected Cyclopentenone | Alkenylzirconium Reagent of Example | Prostaglandin analogs |
|---|---|---|---|
| 28 | Ex. 9 or Ex. 10 | 15 or 17 | nat-1-hydroxymethyl-1,9-dioxo-16RS—hydroxy-16-methylprost-13-trans-ene and ent-1-hydroxymethyl-1,9-dioxo-16RS—hydroxy-16-methylprost-13-trans-ene |
| 29 | Ex. 9 or Ex. 10 | 18 or 23 | nat-1-hydroxymethyl-1,9-dioxo-16RS—hydroxy-16-cyclopropylprost-13-trans-ene and ent-1-hydroxymethyl-1,9-dioxo-16-RS—hydroxy-16-cyclopropylprost-13-trans-ene |
| 30 | Ex. 9 or Ex. 10 | 20 or 25 | nat-1-hydroxymethyl-1,9-dioxo-16RS—hydroxy-16-vinylprost-13-trans-ene and ent-1-hydroxymethyl-1,9-dioxo-16RS—hydroxy-16-cyclopropylprost-13-trans-ene |
| 31 | Ex. 11 or 12 | 15 or 17 | nat-1-hydroxymethyl-1,9-dioxo-16RS—hydroxy-16-methylprosta-5-cis-13-trans-diene and ent-1-hydroxymethyl-1,9-dioxo-16RS—hydroxy-16-methylprosta-5-cis-13-trans-diene |
| 32 | Ex. 11 or 12 | 18 or 23 | nat-1-hydroxymethyl-1,9-dioxo-16RS—hydroxy-16-cyclopropylprosta-5-cis-13-trans-diene and ent-1-hydroxymethyl-1,9-dioxo-16RS—hydroxy-16-cyclopropyl prosta-5-cis,13-trans-diene |
| 33 | Ex. 11 or 12 | 20 or 25 | nat-1-hydroxymethyl-1,9-dioxo-16RS—hydroxy-16-vinylprosta-5-cis,13-trans diene and ent-1-hydroxymethyl-1,9-dioxo-16RS—hydroxy-16-vinylprosta-5-cis,13-trans diene |
| 34 | Ex. 13, 14 or IIIb | 15 or 17 | 1-hydroxymethyl-1,9-dioxo-11R,16S—dihydroxy-16-methylprosta-5-cis,13-trans-diene and 1-hydroxymethyl-1,9-dioxo-11R,16R—dihydroxy-16-methylprosta-5-cis,13-trans-diene |
| 35 | Ex. 13, 14 or IIIb | 16 or 22 | 1-hydroxymethyl-1,9-dioxo-11R,16S—dihydroxy-17,17-dimethylprosta-5-cis,13-trans-diene and 1-hydroxymethyl-1,9-dioxo-11R,16R—dihydroxy-17,17-dimethylprosta-5-cis,13-trans-diene |
| 36 | Ex. 13, 14 or IIIb | 18 or 23 | 1-hydroxymethyl-1,9-dioxo-11R,16S—dihydroxy-16-cyclopropylprosta-5-cis,13-trans-diene and 1-hydroxymethyl-1,9-dioxo-11R,16R—dihydroxy-16-cyclopropylprosta-5-cis,13-trans-diene |
| 37 | Ex. 13, 14 or IIIb | 19 or 24 | 1-hydroxymethyl-1,9-dioxo-11R,16S—dihydroxy-16-(1-propenyl)prosta-5-cis,13-trans-diene and 1-hydroxymethyl-1,9-dioxo-11R,16R—dihydroxy-16-(1-propenyl)prosta-5-cis,13-trans-diene |
| 38 | Ex. 13, 14 or IIIb | 20 or 25 | 1-hydroxymethyl-1,9-dioxo 11R,16S—dihydroxy-16-vinyl-prosta-5-cis,13-trans-diene and 1-hydroxymethyl-1,9-dioxo-11R,16R—dihydroxy-16-vinyl-prosta-5-cis,13-trans-diene |
| 39 | Ex. 13, 14 or IIIb | 21 or 26 | 1-hydroxymethyl-1,9-dioxo-11R,16S—dihydroxy-16-ethylprosta-5-cis,13-trans-diene and 1-hydroxymethyl-1,9-dioxo-11R,16R—dihydroxy-16-ethylprosta-5-cis,13-trans-diene |
| 40 | Ex. 7, 8 or IIIa | 15 or 17 | 1-hydroxymethyl-1,9-dioxo-11R,16S—dihydroxy-16-methylprost-13-trans-ene and 1-hydroxymethyl-1,9-dioxo-11R,16R—dihydroxy-16-methylprost-13-trans-ene |
| 41 | Ex. 7, 8 or IIIa | 16 or 22 | 1-hydroxymethyl-1,9-dioxo-11R,16S—dihydroxy-17,17-dimethylprost-13-trans-ene and 1-hydroxymethyl-1,9-dioxo-11R,16R—dihydroxy-17,17-dimethylprost-13-trans-ene |
| 42 | Ex. 7, 8 or IIIa | 18 or 23 | 1-hydroxymethyl-1,9-dioxo-11R,16S—dihydroxy-16-cyclopropylprost-13-trans-ene and 1-hydroxymethyl-1,9-dioxo-11R,16R—dihydroxy-16-cyclopropyl-prost-13-trans-ene |
| 43 | Ex. 7, 8 or IIIa | 19 or 24 | 1-hydroxymethyl-1,9-dioxo-11R,16S—dihydroxy-16-(1-propenyl)prost-13-trans-ene and 1-hydroxymethyl-1,9 dioxo-11R,16R—dihydroxy-16-(1-propenyl)prost-13-trans-ene |

TABLE VI-continued

Prostaglandin Analogs

| Ex. | Protected Cyclo-pentenone | Alkenyl-zirconium Reagent of Example | Prostaglandin analogs |
|---|---|---|---|
| 44 | Ex. 7, 8 or IIIa | 20 or 25 | 1-hydroxymethyl-1,9-dioxo-11R,16S—dihydroxy-16-vinyl-prost-13-trans-ene and 1-hydroxymethyl-1,9-dioxo-11R,16R—dihydroxy-16-vinylprost-13-trans-ene |
| 45 | Ex. 7, 8 or IIIa | 21 or 26 | 1-hydroxymethyl-1,9-dioxo-11R,16R—dihydroxy-16-ethyl-prost-13-trans-ene and 1-hydroxymethyl-1,9-dioxo-11R,16R—dihydroxy-16-ethylprost-13-trans-ene |
| 46 | IVc | 15 or 17 | methyl 9-oxo-11R,16S—dihydroxy-16-methylprost-13-trans-enoate and methyl 9-oxo-11R,16R—dihydroxy-16-methylprost-13-trans-enoate |
| 47 | IVc | 18 or 23 | methyl 9-oxo-11R,16S—dihydroxy-16-cyclopropylprost-13-trans-enoate and methyl 9-oxo-11R,16R—dihydroxy-16-cyclopropylprost-13-trans enoate |
| 48 | IVc | 20 or 25 | methyl-9-oxo-11R,16S—dihydroxy-16-vinylprost-13-trans-enoate and methyl 9-oxo-11R,16R—dihydroxy-16-vinyl-prost-13-trans-enoate |
| 49 | IVd | 15 or 17 | methyl 9-oxo-11R,16S—dihydroxy-16-methyl-prosta-5-cis,13-trans-dienoate and methyl 9-oxo-11R,16R—dihydroxy-16-methyl-prosta-5-cis,13-trans-dienoate |
| 50 | IVd | 18 or 23 | methyl 9-oxo-11R,16S—dihydroxy-16-cyclopropylprosta-5-cis,13-trans-dienoate and methyl 9-oxo-11R,16R—dihydroxy-16-cyclopropyl-prosta-5-cis,13-trans-dienoate |
| 51 | IVd | 20 or 25 | methyl 9-oxo-11R,16S—dihydroxy-16-vinylprosta-5-cis,13-trans-dienoate and methyl 9-oxo-11R,16R—dihydroxy-16-vinylprosta-5-cis,13-trans-enoate |
| 52 | IVe | 15 or 17 | methyl nat-9-oxo-16RS—hydroxy-16-methyl-prost-13-trans-enoate and methyl ent-9-oxo-16RS—hydroxy-16-methyl-prost-13-trans-enoate |
| 53 | IVe | 18 or 23 | methyl nat-9-oxo-16RS—hydroxy-16-cyclopropyl-prost-13-trans-enoate and methyl ent-9-oxo-16RS—hydroxy-16-cyclopropyl-prost-13-trans-enoate |
| 54 | IVe | 20 or 25 | methyl nat-9-oxo-16RS—hydroxy-16-vinyl-prost-13-trans-enoate and methyl ent-9-oxo-16RS—hydroxy-16-vinyl-prost-13-trans-enoate |
| 55 | IVf | 15 or 17 | methyl nat-9-oxo-16RS—hydroxy-16-methyl-prosta-5-cis-13-trans-dienoate and methyl ent-9-oxo-16RS—hydroxy-16-methyl-prosta-5-cis,13-trans-dienoate |
| 56 | IVf | 18 or 23 | methyl nat-9-oxo-16RS—hydroxy-16-cyclopropyl-prosta-5-cis-13-trans-dienoate and methyl ent-9-oxo-16RS—hydroxy-16-cyclopropyl-prosta-5-cis,13-trans-dienoate |
| 57 | IVf | 20 or 25 | methyl nat-9-oxo-16RS—hydroxy-16-vinylprosta-5-cis,13-trans-dienoate and methyl ent-9-oxo-16RS—hydroxy-16-vinylprosta-5-cis,13-trans-dienoate |
| 58 | IVh | 15 or 17 | 1-hydroxymethyl-1,9-dioxo-11R,16S—dihydroxy-16-methyl-prosta-5-cis,13-trans-diene 1-ethylene ketal and 1-hydroxymethyl-1,9-dioxo-11R,16R—dihydroxy-16-methylprosta-5-cis,13-trans-diene 1-ethylene ketal |
| 59 | IVh | 18 or 23 | 1-hydroxymethyl-1,9-dioxo-11R,16S—dihydroxy-16-cyclopropyl-prosta-5-cis,13-trans-diene 1-ethylene ketal and 1-hydroxy methyl-1,9-dioxo-11R,16R—dihydroxyl-16-cyclopropylprosta-5-cis,13-trans-diene 1-ethylene ketal |
| 60 | IVh | 20 or 25 | 1-hydroxymethyl-1,9-dioxo-11R,16S—dihydroxy-16-vinyl-prosta-5-cis,13-trans-diene 1-ethylene ketal and 1-hydroxymethyl-1,9-dioxo-11R,16R—dihydroxy-16-vinylprosta-5-cis,13-trans-diene 1-ethylene ketal |
| 61 | IVg | 15 or 17 | nat-1-hydroxymethyl-1,9-dioxo-16RS—hydroxy-16-methyl-prost-13-trans-ene 1-ethylene ketal and ent-1-hydroxymethyl-1,9-dioxo-16RS—hydroxy-16-methyl-prost-13-trans-ene |
| 62 | IVg | 18 or 23 | nat-1-hydroxymethyl-1,9-dioxo-16RS—hydroxy-16-cyclopropylprost-13-trans-ene 1-ethylene ketal and ent-1-hydroxymethyl-1,9-dioxo-16RS—hydroxy-16-cyclopropylprost-13-trans-ene |
| 63 | IVg | 20 or 25 | nat-1-hydroxymethyl-1,9-dioxo-16RS—hydroxy-16-vinyl-prost-13-trans-ene and ent-1-hydroxymethyl-1,9-dioxo-16RS—hydroxy-16-vinylprost-13-trans-ene |

This invention has been described in terms of specific embodiments set forth in detail herein, but it should be understood that these are by way of illustration only and that the invention is not necessarily limited thereto. Modifications and variations will be apparent from the disclosure and may be resorted to without departing from the spirit of this invention, as those skilled in the art will understand. Accordingly, such variations and modifications of the disclosed invention are considered to be within the scope of this invention and the following claims.

What is claimed is:

1. A compound of the formula:

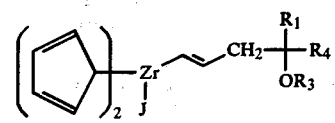

wherein J is bromo or chloro, $R_1$ is methyl, ethyl, 1-propenyl, vinyl or cyclopropyl; $R_4$ is an alkyl radical of 2-7 carbon atoms and $R_3$ is a hydroxyl-protecting group.

2. The compound of claim 1 wherein J is chloro.

3. The compound of claim 2 wherein $R_1$ is 1-propenyl.

4. The compound of claim 2 wherein $R_1$ is methyl.

5. The compound of claim 2 wherein $R_1$ is ethyl.

6. The compound of claim 2 wherein $R_1$ is cyclopropyl.

7. The compound of claim 2 wherein $R_1$ is vinyl.

8. The compound according to claim 4, 6 or 7 wherein $R_4$ is a $C_4$-alkyl group.

9. The compound according to claim 8 wherein $R_4$ is n-butyl.

10. The compound of claim 4, 6 or 7 wherein $R_3$ is a $C_1$–$C_4$ trialkylsilyl group.

11. The compound of claim 10 wherein the trialkylsilyl group is trimethylsilyl.

12. The compound of claim 10 wherein the trialkylsilyl group is triethylsilyl.

13. The compound of claim 2 wherein $R_1$ is methyl, ethyl, cyclopropyl, vinyl or 1-propenyl, $R_3$ is trimethylsilyl or triethylsilyl, and $R_4$ is n-butyl.

14. A compound according to claim 2 which is chloro-bis($\eta^5$-2,4-cyclopentadien-1-yl)-(4-methyl-4-triethylsiloxy-1-trans-octenyl)zirconium.

15. A compound according to claim 2 which is chloro-bis($\eta^5$-2,4-cyclopentadien-1-yl)-(4-methyl-4-trimethylsiloxy-1-trans-octenyl)zirconium.

16. A compound according to claim 2 which is chloro-bis ($\eta^5$-2,4-cyclopentadien-1-yl)-(5,5-dimethyl-4-trimethylsiloxy-1-trans-octenyl)zirconium.

17. A compound according to claim 2 which is chloro-bis($\eta^5$-2,4-cyclopentadien-1-yl)-(5,5-dimethyl-4-triethylsiloxy-1-trans-octenyl)zirconium.

18. A compound according to claim 2 which is chloro-bis($\eta^5$-2,4-cyclopentadien-1-yl)-(4-cyclopropyl-4-trimethylsiloxy-1-trans-octenyl)zirconium.

19. A compound according to claim 2 which is chloro-bis($\eta^5$-2,4-cyclopentadien-1-yl)-(4-cyclopropyl-4-triethylsiloxy-1-trans-octenyl)zirconium.

20. A compound according to claim 2 which is chloro-bis($\eta^5$-2,4-cyclopentadien-1-yl)-[4-(1-propenyl)-4-trimethylsiloxy-1-trans-octenyl]zirconium.

21. A compound according to claim 2 which is chloro-bis($\eta^5$-2,4-cyclopentadien-1-yl)-[4-(1-propenyl)-4-triethylsiloxy-1-trans-octenyl]zirconium.

22. A compound according to claim 2 which is chloro-bis($\eta^5$-2,4-cyclopentadien-1-yl)-(4-vinyl-4-trimethylsiloxy-1-trans-octenyl)zirconium.

23. A compound according to claim 2 which is chloro-bis($\eta^5$-2,4-cyclopentadien-1-yl)-(4-vinyl-4-triethylsiloxy-1-trans-octenyl)zirconium.

24. A compound according to claim 2 which is chloro-bis($\eta^5$-cyclopentadien-1-yl)-(4-ethyl-4-trimethylsiloxy-1-trans-octenyl)zirconium.

25. A compound according to claim 2 which is chloro-bis($\eta^5$-cyclopentadien-1-yl)-(4-ethyl-4-triethylsiloxy-1-trans-octenyl)zirconium.

26. The compound according to claim 1 wherein $R_3$ is selected from the group consisting of tetrahydropyranyl, 1-ethoxyethyl or $C_1$–$C_4$ trialkylsilyl.

27. The compound according to claim 1 wherein the hydroxyl group is removable by exposure to dilute aqueous acid.

* * * * *